(12) United States Patent
Filiberti

(10) Patent No.: US 9,440,094 B2
(45) Date of Patent: Sep. 13, 2016

(54) TREATMENT COUCH FOR SMALL ISOCENTRIC ROTATIONS

(71) Applicant: Varian Medical Systems International AG, Zug (CH)

(72) Inventor: Reto W. Filiberti, Steinhausen (CH)

(73) Assignee: VARIAN MEDICAL SYSTEMS INTERNATIONAL AG, Zug (CH)

(*) Notice: Subject to any disclaimer, the term of this patent is extended or adjusted under 35 U.S.C. 154(b) by 274 days.

(21) Appl. No.: 13/831,648

(22) Filed: Mar. 15, 2013

(65) Prior Publication Data

US 2014/0275697 A1  Sep. 18, 2014

(51) Int. Cl.
*A61N 5/10* (2006.01)
*A61G 13/04* (2006.01)

(52) U.S. Cl.
CPC .............. *A61N 5/107* (2013.01); *A61N 5/1037* (2013.01); *A61N 5/1081* (2013.01)

(58) Field of Classification Search
CPC ................... A61N 5/1049; A61N 2005/1061; A61N 5/1067; A61N 5/107; A61N 2005/1051; A61N 2005/1059; A61N 2005/1063; A61N 5/1037; A61N 5/1081; A61B 6/0407; A61B 6/0457; A61B 6/06; A61B 6/027; A61B 6/032
See application file for complete search history.

(56) References Cited

U.S. PATENT DOCUMENTS 6,986,179 B2 * 1/2006 Varadharajulu et al. .......... 5/611
2005/0234327 A1 * 10/2005 Saracen et al. ............... 600/407

* cited by examiner

*Primary Examiner* — Christine H Matthews
*Assistant Examiner* — Joshua D Lannu
(74) *Attorney, Agent, or Firm* — Patent Law Group LLP; David C. Hsia

(57) ABSTRACT

A treatment system for a patient includes a treatment couch to position the patient. The treatment couch includes a couch top and one or more stages to pitch the couch top about a lateral axis and/or roll the couch top about a longitudinal axis, translate the couch top along lateral directions and/or longitudinal directions, rotate the couch top about a vertical axis, and translate the couch top along vertical directions.

14 Claims, 6 Drawing Sheets

TREATMENT COUCH FOR SMALL ISOCENTRIC ROTATIONS

CROSS REFERENCE TO RELATED APPLICATION

This application is related to U.S. patent application Ser. No. 13/090,592, filed Apr. 20, 2011, which is incorporated by reference in its entirety.

BACKGROUND

Radiotherapy, also known as radiation oncology, is the medical use of ionizing radiation to destroy cancer cells in a malignant tumor. The goal of radiotherapy is to destroy as many cancer cells as possible while limiting harm to surrounding healthy tissue.

FIG. 1 shows a side view of a conventional treatment system 100. System 100 includes a gantry 102 that positions a radiation delivery apparatus 104 around a patient during radiation therapy. The patient is positioned by a treatment couch 106. The combination of gantry and couch movements provides greater flexibility in delivering the ionizing radiation to the patient.

In FIG. 1, all movements are shown at their zero positions except for the vertical displacement and the longitudinal displacement of treatment couch 106. Gantry 102 is mounted via a bearing to a stand 103 that is fixed to a floor 108. Gantry 102 can rotate radiation delivery apparatus 104 about a horizontal axis 110, thereby defining a radiation isocenter 112 where the radiation beams meet in space. Treatment couch 106 has a turntable 114 fixed to floor 108 so it can rotate isocentrically about a vertical axis 116 passing through isocenter 112. Treatment couch 106 has a couch top 118 that can rotate eccentrically relative to turntable 112 about a vertical axis 120. FIG. 2 shows a top view of treatment couch 106 with couch top 118 at the zero position of the isocentric rotation about vertical axis 116, and FIG. 3 shows a top view of treatment couch 106 with couch top 118 after an isocentric rotation about vertical axis 116. Referring back to FIG. 1, couch top 118 can also translate vertically along vertical axis 120, translate laterally in lateral directions 124, and translate longitudinally in longitudinal directions 122.

BRIEF DESCRIPTION OF THE DRAWINGS

In the drawings.

Use of the same reference numbers in different figures indicates similar or identical elements.

DETAILED DESCRIPTION OF THE INVENTION

Figure 1:
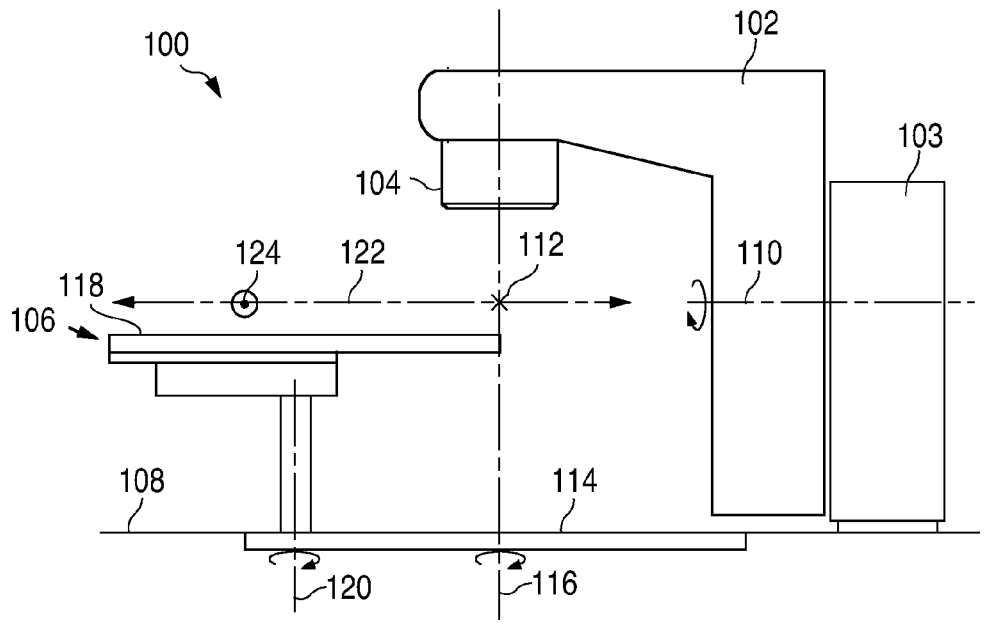
FIG. 1 shows a side view of a conventional treatment system.

In FIG. 1, treatment couch 106 is constructed so it can be rotated isocentrically over a large range of angles, typically more than ±90 degrees. Isocentric rotation is handled by turntable 114 in floor 108 and translated up to the rest of the treatment couch 106. This arrangement avoids placing any rotation mechanism, such as bearings and actuators, in the treatment path when gantry 102 rotates radiation delivery apparatus 104 to a six o'clock position to treat the patient from underneath. However, this approach creates a heavy, bulky, and expensive structure. Furthermore, even a small isocentric rotation involves the rotation of the entire treatment couch 106.

In examples of the present disclosure, a rotation point of a couch top is offset from an isocenter towards the back of the couch top. Lateral and longitudinal displacements of the couch top are compensated by translating the couch top laterally and longitudinally. This arrangement places any rotation mechanism outside of the radiation field for the entire longitudinal travel of the couch top to avoid any interference with the radiation beams. This arrangement also removes the need for a turntable.

Figure 4:
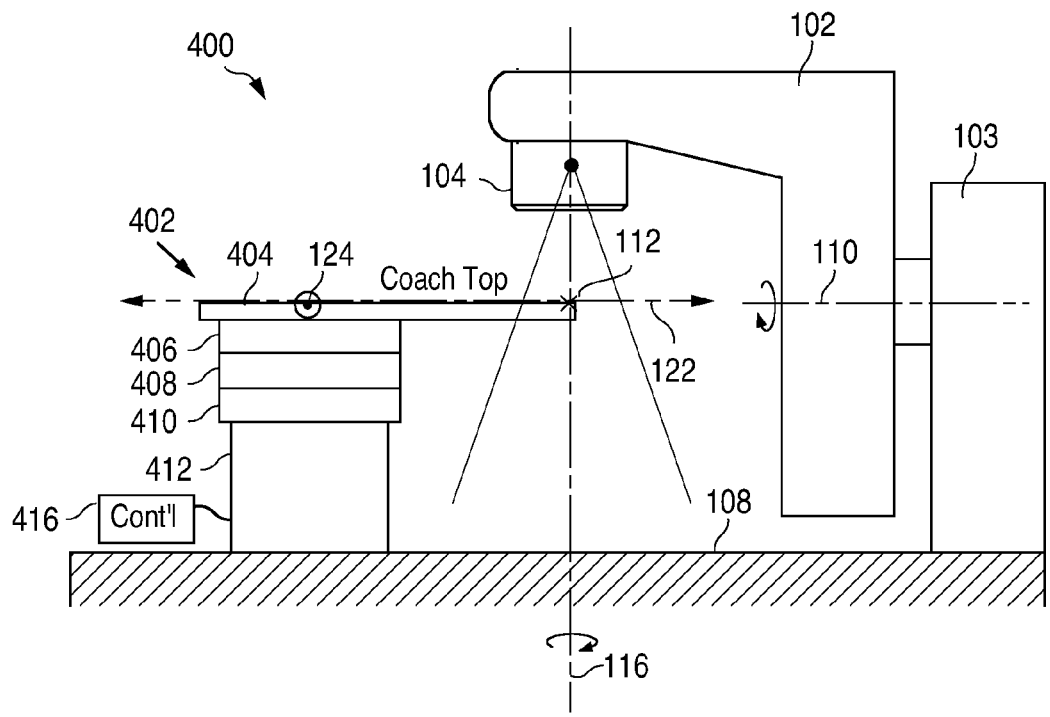
FIG. 4 shows a side view of a treatment system in one example of the present disclosure.
Figure 2:
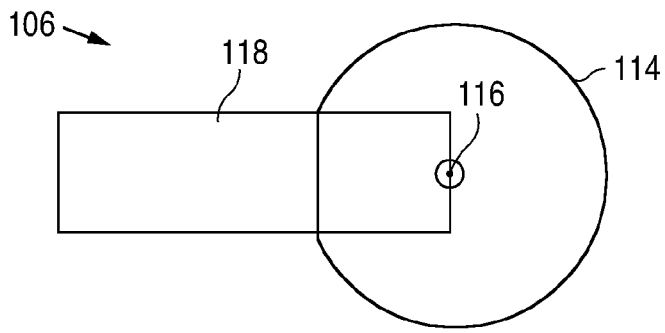
FIGS. 2 and 3 show top views of an isocentric rotation of a conventional treatment couch in the conventional treatment system of FIG. 1.

FIG. 4 shows a side view of a treatment system 400 in one example of the present disclosure. System 400 includes gantry 102 that positions radiation delivery apparatus 104 around a patient during radiation therapy. The patient is positioned by a treatment couch 402 with multiple degrees of freedom.

In FIG. 4, all movements are shown at their zero positions except for the longitudinal displacement of treatment couch 402. Gantry 102 is mounted via a bearing to stand 103 that is fixed to floor 108. Gantry 102 can rotate radiation delivery apparatus 104 about horizontal axis 110, thereby defining radiation isocenter 112. Treatment couch 402 includes a couch top 404, a pitch and roll stage 406, an angular stage 408, a lateral and longitudinal stage 410, and a vertical stage 412.

Figure 5:
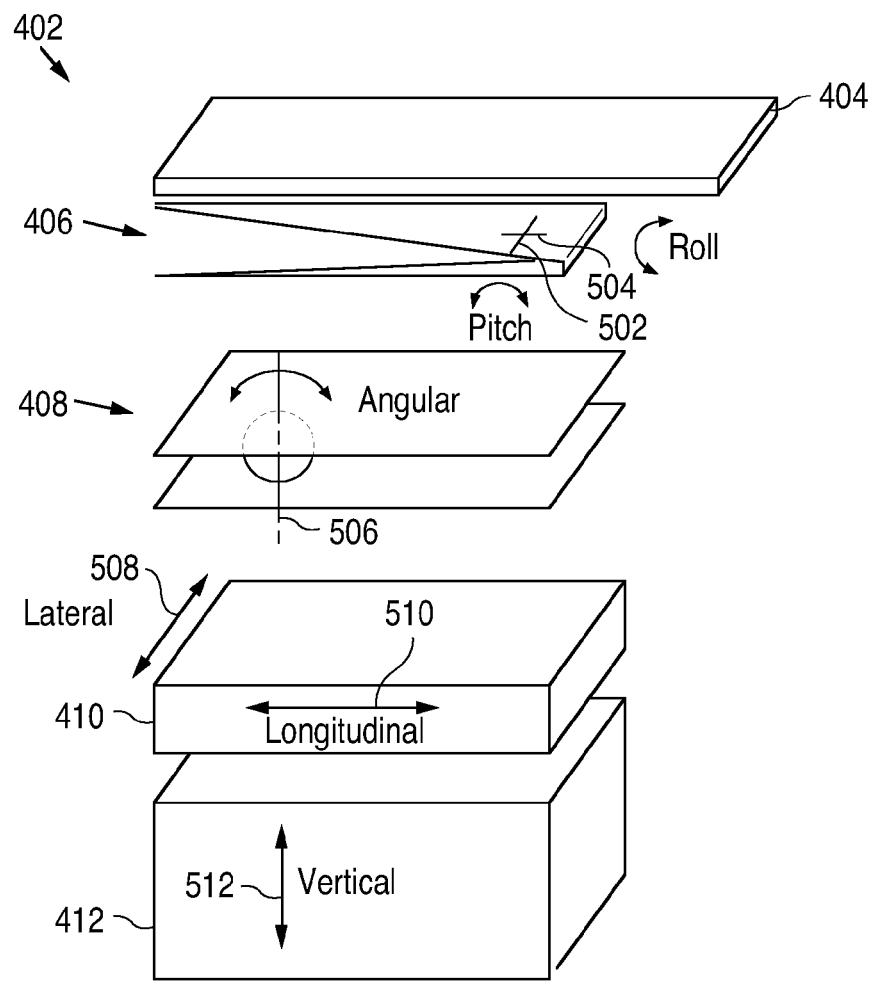
FIG. 5 shows an exploded view of a treatment couch in the treatment system of FIG. 4 in one example of the present disclosure.

FIG. 5 shows an exploded view of treatment couch 402 in one example of the present disclosure. Pitch and roll stage 406 is to pitch couch top 404 about a lateral axis 502, and roll couch top 404 about a longitudinal axis 504. Pitch and roll stage 406 may be used for a variety of purposes, including compensating for any deflection in couch top 404, minor patient misalignments, or slight tumor rotations. An example of pitch and roll stage 406 is described in U.S. patent application Ser. No. 13/090,592 filed Apr. 20, 2011, which is incorporated by reference in its entirety.

Angular stage 408 is to rotate couch top 404 about a vertical axis 506. Lateral and longitudinal stage 410 is to translate along lateral directions 508 and longitudinal directions 510, thereby translating couch top 404 along lateral directions 124 (FIG. 4) and longitudinal directions 122 (FIG. 4). Note that directions may be parallel with or coincide with an axis of the same orientation. Vertical stage 412 is to translate couch top 404 along vertical directions 512. In one example, vertical stage 412 is fixed to floor 108 (FIG. 4), lateral and longitudinal stage 410 is mounted on vertical stage 412, angular stage 408 is mounted on lateral and longitudinal stage 410, pitch and roll stage 406 is mounted on angular stage 408, and couch top 404 is mounted on pitch and roll stage 406.

Figure 3:
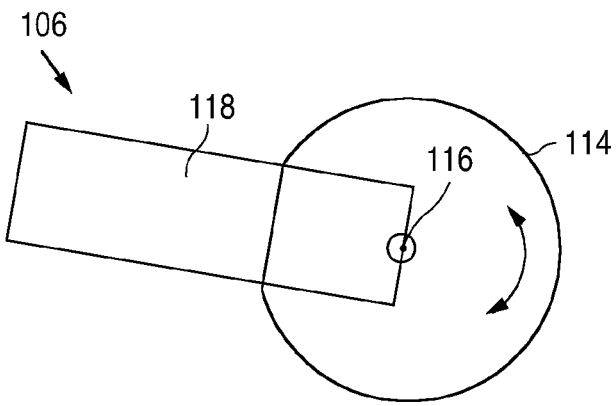
Figure 6:
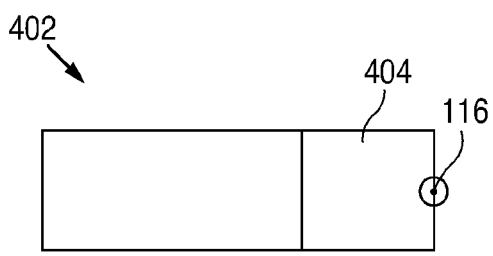
FIGS. 6 and 7 show top views of an isocentric rotation of the treatment couch of FIG. 4 in one example of the present disclosure.
Figure 7:
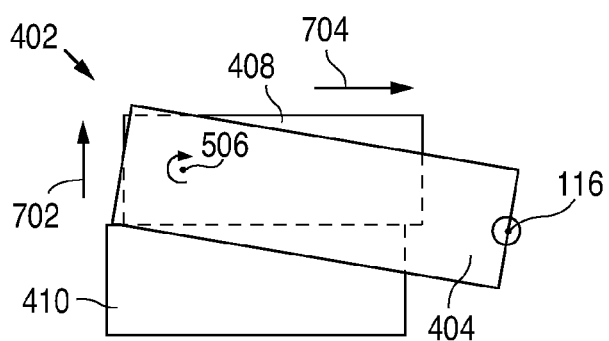

Referring back to FIG. 4, treatment system 400 further includes a controller 416 for treatment couch 402. During treatment, controller 416 may programmed to cause stages 406, 408, 410, and 412 to provide motion to couch top 404 on two or more axes simultaneously during a radiation treatment in order to compensate for tumor motions or follow a dynamic treatment plan. Controller 416 is programmed to perform any small isocentric rotation of couch top 404 about vertical axis 116 by simultaneously rotating angular stage 408 about vertical axis 506 (FIG. 5) and translating lateral and longitudinal stage 410 along lateral directions 508 (FIG. 5) and longitudinal directions 510 (FIG. 5). A small isocentric rotation may be an isocentric rotation less than or equal to 45 degrees. FIG. 6 shows treatment couch 402 with couch top 404 at the zero position of the isocentric rotation, and FIG. 7 shows couch top 404 after a small clockwise isocentric rotation performed with a clockwise eccentric rotation of angular stage 408 about vertical axis 506, a lateral displacement 702 of lateral and longitudinal stage 410 in a lateral direction 508 (FIG. 5) away from vertical axis 116, and a longitudinal displacement 704 of lateral and longitudinal stage 410 in a longitudinal direction 510 (FIG. 5) toward vertical axis 116. Note that the isocentric rotation of FIG. 7 achieved with angular stage 408 and lateral and longitudinal stage 410 is the same as the isocentric rotation of FIG. 3 achieved with turntable 114.

Figure 8:
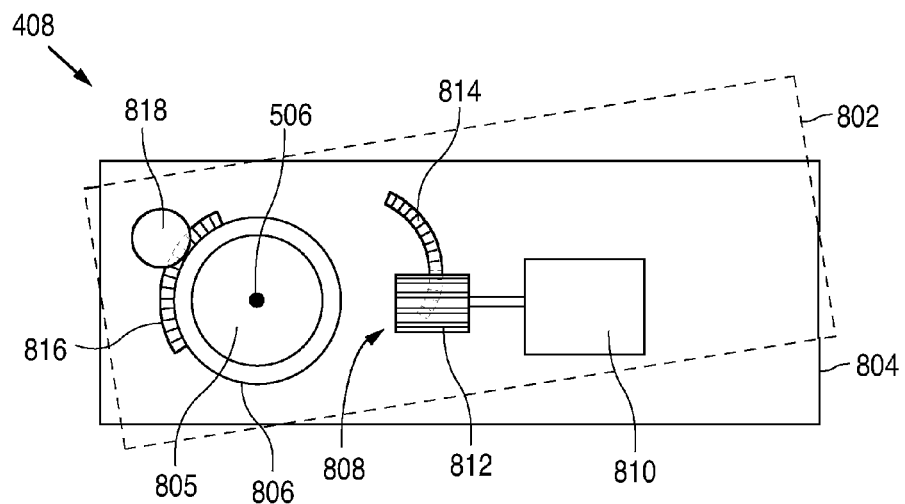
FIGS. 8 and 9 show top and side views of an angular stage of the treatment couch of FIG. 4 in one example of the present disclosure.
Figure 9:
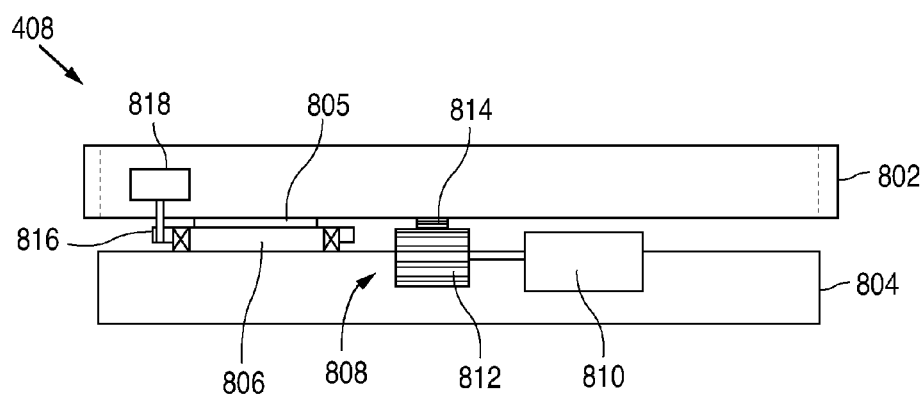

FIGS. 8 and 9 show top and side views of an angular stage 408 in one example of the present disclosure. Angular stage 408 includes a top 802 (shown in phantom) and a base 804. Top 802 includes an axle 805 received in a bearing 806 mounted to base 804 so top 802 can rotate about vertical axis 506. Angular stage 408 also includes a drive mechanism 808 that rotates top 802. Drive mechanism 808 includes a motor 810 with a pinion 812, and a curved rack 814. Motor 810 is mounted on base 804 with pinion 812 engaging curved rack 814, which is mounted on the backside of top 802. Angular stage 408 further includes a curved readout rack 816 and one or more readout sensors 818. Curved readout rack 816 is mounted to the side of bearing 806, and readout sensor 818 is mounted to the backside of top 802 to engage rack 816. Readout sensor 818 reads the rotational position angular stage 408 and feeds the information to controller 416 (FIG. 4). Note that the rotation mechanisms of angular stage 408, such as and bearing 806 and drive mechanism 808, are located outside of a radiation field of radiation delivery apparatus 104 (FIG. 4) for the entire longitudinal travel couch top 404 (FIG. 4) to avoid any interference with the radiation beams.

Figure 10:
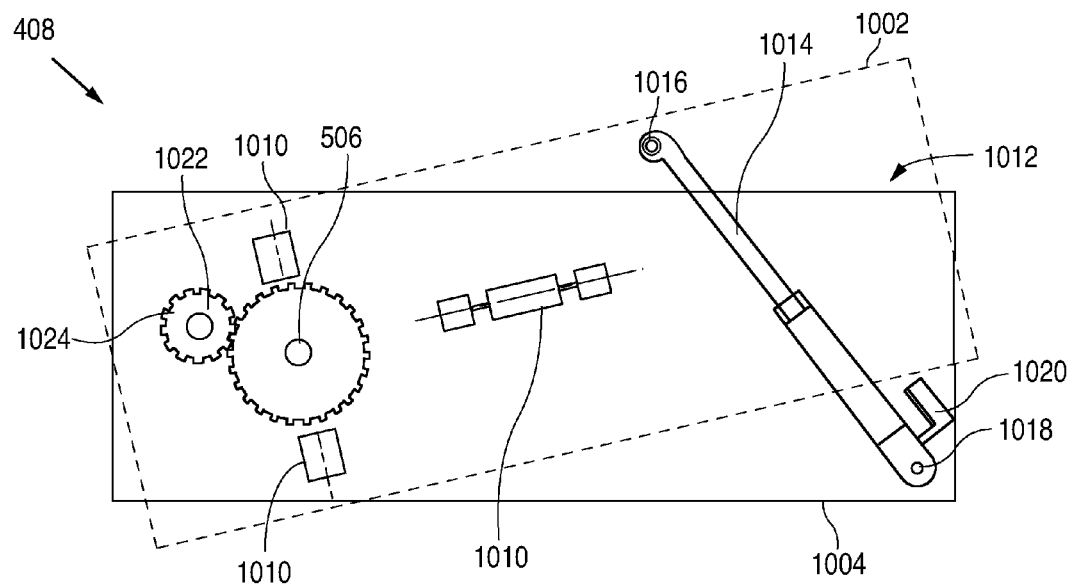
FIGS. 10 and 11 show top and side views of another angular stage of the treatment couch of FIG. 4 in another example of the present disclosure.
Figure 11:
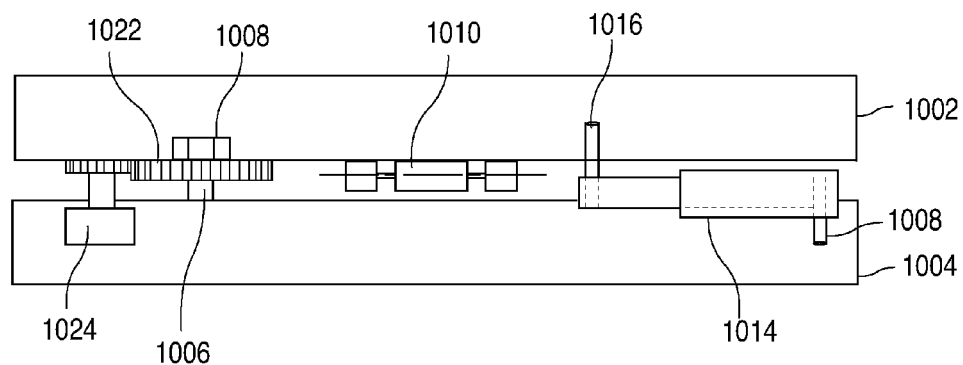

FIGS. 10 and 11 show top and side views of angular stage 408 in another example of the present disclosure. Angular stage 408 includes a top 1002 (shown in phantom) and a base 1004. Base 1004 includes an axel 1006 (FIG. 11) received in a bearing 1008 (FIG. 11) mounted to top 1002 so top 1002 can rotate about vertical axis 506. Angular stage 408 also includes support rollers 1010 between top 1002 and base 1004. Support rollers 1010 may have shafts supported by bearings.

Angular stage 408 includes a drive mechanism 1012 that rotates top 1002. Drive mechanism 1012 includes a linear actuator 1014 having an upper actuator joint 1016 pivotally fixed to top 1002 and a lower actuator joint 1018 pivotally fixed to base 1004. Linear actuator 1014 includes a motor 1020 (FIG. 10) that extends and retracts the linear actuator.

Angular stage 408 includes one or more readout cog wheels 1022 and one or more readout sensors 1024. Readout cog wheel 1022 is mounted to the backside of top 1002 and centered on vertical axis 506. Readout sensor 1024 is mounted to base 1004 to engage readout cog wheel 1022. Readout sensor 1024 reads the rotational position angular stage 408 and feeds the information to controller 416 (FIG. 4).

Note that the rotation mechanisms of angular stage 408, such as bearing 1008, support rollers 1010, and drive mechanism 1012, are located outside of a radiation field of radiation delivery apparatus 104 (FIG. 4) for the entire longitudinal travel couch top 404 (FIG. 4) to avoid any interference with the radiation beams.

Although two examples of angular stage 408 are shown, angular stage 408 may be implemented with other mechanisms including chain drive, belt drive, band drive, string or cord drive.

Figure 12:
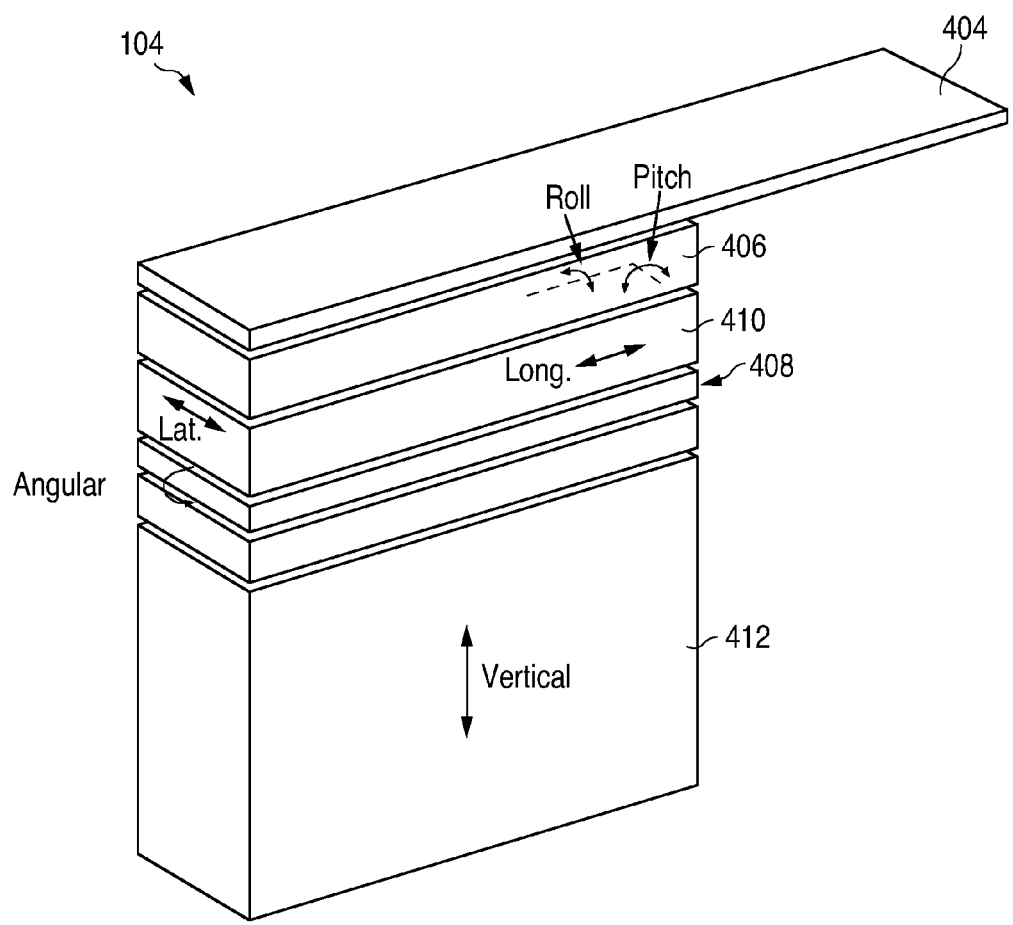
FIG. 12 shows an isometric view of another treatment couch in the treatment system of FIG. 4 in one example of the present disclosure.

FIG. 12 shows an isometric view of treatment couch 402 in a different configuration in one example of the present disclosure. Treatment couch 402 includes couch top 404, pitch and roll stage 406, angular stage 408, lateral and longitudinal stage 410, and vertical stage 412. Unlike the configuration shown in FIGS. 4 and 5, angular stage 408 is mounted on vertical stage 412, lateral and longitudinal stage 410 is mounted on angular stage 408, and pitch and roll stage 406 is mounted on lateral and longitudinal stage 410. Another configuration of treatment couch 402 may arrange the various stages in a different order.

Various other adaptations and combinations of features of the examples disclosed are within the scope of the invention. For example, one or more of the stages in treatment couch 402 may be omitted. In one example, pitch and roll stage 406 is omitted to reduce cost. Similarly, multiple stages may be combined into one stage, or a stage having multiple motions may be split into multiple stages each having lesser than all of the motions, and still practice the isocentric rotation described above. Numerous examples are encompassed by the following claims.

The invention claimed is:

1. A treatment system for a patient, comprising:
   a radiation delivery apparatus;
   a gantry configured to rotate the radiation delivery apparatus about a horizontal axis, thereby defining an isocenter; and
   a treatment couch to position the patient, comprising:
      a couch top;
      a pitch and roll stage configured to pitch and roll the couch top about pitch and roll axes;
      a lateral and longitudinal translation stage to translate the couch top along lateral and longitudinal translation axes;
      an angular stage to rotate the couch top about a first vertical rotation axis; and
      a vertical stage to translate the couch top along a vertical translation axis; and
   a controller programmed to perform a rotation of the treatment couch about a second vertical rotation axis by dynamically moving both the angular stage and the lateral and longitudinal translation stage to rotate the couch top about the first vertical rotation axis and translate the couch top along the lateral and the longitudinal translational axes, wherein the first vertical rotation axis is proximal to a first end of the couch top away from the radiation delivery apparatus, and the second vertical axis is proximal to a second end of the couch top near the radiation delivery apparatus.

2. The treatment system of claim 1, wherein the controller is programmed to provide motion to the couch top on two or more axes simultaneously during a radiation treatment in order to compensate for tumor motions or follow a dynamic treatment plan.

3. The treatment system of claim 1, wherein the angular stage comprises rotation mechanisms located outside of a radiation field of the radiation delivery apparatus for an entire longitudinal travel of the couch top.

4. The treatment system of claim 1, wherein:
the vertical stage is fixed to a floor;
the angular stage is mounted on the vertical stage;
the lateral and longitudinal translation stage is mounted on the angular stage;
the pitch and roll stage is mounted on the lateral and longitudinal translation stage; and
the couch top is mounted on the pitch and roll stage.

5. The treatment system of claim 1, wherein:
the vertical stage is fixed to a floor;
the lateral and longitudinal translation stage is mounted on the vertical stage;
the angular stage is mounted on the lateral and longitudinal translation stage;
the pitch and roll stage is mounted on the angular stage; and
the couch top is mounted on the pitch and roll stage.

6. The treatment system of claim 1, wherein an individual axis includes one or more readout sensors.

7. The treatment system of claim 1, wherein the second vertical rotation axis passes through the isocenter.

8. A treatment system for a patient, comprising:
a treatment couch to position the patient, comprising:
  a couch top; and
  one or more stages to:
    pitch the couch top about a lateral axis or roll the couch top about a longitudinal axis;
    translate the couch top along lateral and longitudinal directions;
    rotate the couch top about a vertical axis; and
    translate the couch top along vertical directions;
wherein:
  the one or more stages include an angular stage to rotate the coach top about the vertical axis; and
  the angular stage comprises:
    a base;
    a top rotatably coupled to the base; and
    a drive mechanism to rotate the top relative to the base about the vertical axis, the drive mechanism comprising:
      a motor mounted to the base, the motor comprising a pinion; and
      a curved rack mounted to the top and engaged to the pinion.

9. A treatment system for a patient, comprising:
a treatment couch to position the patient, comprising:
  a couch top; and
  one or more stages to:
    pitch the couch top about a lateral axis or roll the couch top about a longitudinal axis;
    translate the couch top along lateral and longitudinal directions;
    rotate the couch top about a vertical axis; and
    translate the couch top along vertical directions;
wherein:
  the one or more stages include an angular stage to rotate the coach top about the vertical axis; and
  the angular stage comprises:
    a base;
    a top rotatably coupled to the base; and
    a drive mechanism to rotate the top relative to the base about the vertical axis, the drive mechanism comprising a linear actuator having a first end pivotally fixed to the top and a second end pivotally fixed to the base.

10. A treatment method comprising:
rotating a couch top about a first vertical rotation axis proximal to a first end of the couch top proximate to a radiation delivery apparatus, comprising:
  rotating with an angular stage, the couch top about a second vertical rotation axis, the second vertical rotation axis being proximal to a second end of the couch top away from the radiation delivery apparatus; and
  translating with a lateral and longitudinal translation stage, the couch top along horizontal lateral and longitudinal axes to compensate for lateral and longitudinal displacements of the first vertical rotation axis cause by said rotating.

11. The method of claim 10, wherein said rotating and said translating occur simultaneously.

12. The method of claim 11, further comprising at least one of pitching the couch top about the horizontal lateral axis and rolling the couch top about the horizontal longitudinal axis to compensate for a deflection in the couch top, patient misalignments, or tumor rotations.

13. The method of claim 10, further comprising providing motion to the couch top on two or more axes simultaneously during a radiation treatment in order to compensate for tumor motions or follow a dynamic treatment plan.

14. The method of claim 10, further comprising rotating a radiation delivery apparatus about a horizontal rotation axis, thereby defining the isocenter, the first vertical rotation axis passing through the isocenter.

* * * * *